United States Patent
O'Reilly et al.

(10) Patent No.: US 9,291,818 B2
(45) Date of Patent: Mar. 22, 2016

(54) SELF-CLEANING OPTICAL SYSTEM

(71) Applicant: University College Dublin, National University of Ireland, Dublin, Dublin (IE)

(72) Inventors: Fergal O'Reilly, Dublin (IE); Kenneth Fahy, Dublin (IE); Paul Sheridan, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 0 days.

(21) Appl. No.: 14/400,354

(22) PCT Filed: May 16, 2013

(86) PCT No.: PCT/EP2013/060146
§ 371 (c)(1),
(2) Date: Nov. 11, 2014

(87) PCT Pub. No.: WO2013/186008
PCT Pub. Date: Dec. 19, 2013

(65) Prior Publication Data
US 2015/0138636 A1    May 21, 2015

(30) Foreign Application Priority Data

Jun. 14, 2012  (IE) .................... S2012/0277

(51) Int. Cl.
*G02B 1/00* (2006.01)
*G02B 27/00* (2006.01)
*G02B 1/11* (2015.01)
*G01N 21/15* (2006.01)

(52) U.S. Cl.
CPC ............ *G02B 27/0006* (2013.01); *G01N 21/15* (2013.01); *G02B 1/11* (2013.01)

(58) Field of Classification Search
CPC ....... G02B 1/10; G02B 27/00; G02B 27/0006; G02B 1/11; G01N 21/15; G03F 7/20; H01L 21/02
USPC ........................................... 359/508
See application file for complete search history.

(56) References Cited

U.S. PATENT DOCUMENTS

| | | |
|---|---|---|
| 3,744,873 A | 7/1973 | Jamison |
| 4,784,491 A | 11/1988 | Penney et al. |
| 5,490,912 A | 2/1996 | Warner et al. |
| 6,628,397 B1 | 9/2003 | Nikoonahad et al. |

(Continued)

FOREIGN PATENT DOCUMENTS

| | | |
|---|---|---|
| EP | 0440026 A1 | 8/1991 |
| WO | 2005075700 A1 | 8/2005 |
| WO | 2009110793 A1 | 9/2009 |

OTHER PUBLICATIONS

Author Unknown, "Products: PLD Intelligent Window," PVD Products, www.pvdproducts.com/products/intelligent_windows.aspx, 2011, accessed Nov. 26, 2014, 3 pages.

(Continued)

*Primary Examiner* — Euncha Cherry
(74) *Attorney, Agent, or Firm* — Withrow & Terranova, P.L.L.C.

(57) ABSTRACT

A self-cleaning optical system for the transmission or reflection of light to and/or from a process region comprises a liquid bath and a transparent or reflective optical component continuously rotatable about a non-vertical axis so that a lower part of the component continuously rotates through the bath. When the component emerges from the bath, a coating of the liquid remains thereon which forms a substantially uniform film on at least a part of the component through which the light is transmitted or from which the light is reflected.

20 Claims, 4 Drawing Sheets

(56) References Cited

U.S. PATENT DOCUMENTS

| | | |
|---|---|---|
| 7,145,145 B2 | 12/2006 | Benson |
| 7,501,145 B2 | 3/2009 | Selvamanickam et al. |
| 2005/0148285 A1* | 7/2005 | Hosoda .................. B08B 1/007 451/5 |

OTHER PUBLICATIONS

Chraplyvy, A. R., "Liquid Surface Coating for Optical Components Used in High Power Laser Applications," Applied Optics, vol. 16, No. 9, Sep. 1977, pp. 2491-2494.

Kessler, F., et al., "Direct a-Si:H and a-SiC:H Photo-CVD Deposition with a $D_2$-Lamp and Dielectric Barrier Discharge Lamp," International Symposium on Plasma Chemistry, Pugnochiuso, Italy, Sep. 1989, pp. 1383-1388.

Pastorino, P., et al., "Amorphous Hydrogenated Silicon Nitride Deposited by Mercury Photosensitization Chemical Vapour Deposition for Optoelectronic Applications," Journal de Physique IV France, vol. 5, No. C5, Jun. 1995, pp. C5-1149-C5-1155.

International Search Report and Written Opinion for PCT/EP2013/060146 mailed Sep. 5, 2013, 9 pages.

\* cited by examiner

SELF-CLEANING OPTICAL SYSTEM

This application is a 35 USC 371 national phase filing of International Application No. PCT/EP2013/060146, filed May 16, 2013, which claims priority to Irish national application S2012/0277, filed Jun. 14, 2012, the disclosures of which are incorporated herein by reference in their entireties.

FIELD OF THE DISCLOSURE

The invention relates to optical systems for use primarily, but not exclusively, in vacuum systems which are prone to spoiling in plasma processing. However, the invention is applicable more generally to any physical, chemical or other process (including vacuum processes involving charged and neutral particles and photons, especially x-rays) where debris from the process can impinge a window whose transparency to light is important. In the context of the present invention, "light" includes UV and IR wavelengths as well as visible wavelengths, and terms such as "optical" and "transparent" are to be interpreted accordingly.

BACKGROUND

Normally in these situations the window is replaced when it becomes too dirty, or some mixture of window replacement, or rotation and gas curtains are used.

In U.S. Pat. No. 7,501,145 the laser power coming through a window in a pulsed laser deposition (PLD) process is monitored inside the chamber in order to adjust the incoming laser energy impinging on the window, which is becoming progressively more opaque, to deliver the same energy to the target material to be sputtered. A disadvantage is that eventually losses through the window are too high to be compensated for. This happens more quickly in systems with high deposition rates.

In WO/2005/0075700 and U.S. Pat. No. 4,784,491 a gas curtain is used to slow and deflect "errant material" from a PLD process away from the laser input window. However, in the case of gas curtains there is a requirement to introduce a gas in to the system in order to produce the gas curtain. This limits the vacuum operating pressure of the system and complicates the system design to make sure that the gas input is sufficient to block the debris effectively, but not too much to alter the process parameters. Also, the gas curtain will still allow some window coating given the mean free paths at vacuum pressures typical in pulsed laser deposition (PLD) and extreme ultra violet (EUV) and other plasma process systems.

In another approach a rotating glass window is used until it's transparency drops below a certain level and a new piece of window is rotated in front of the laser—see, for example, www.pvdproducts.com/products/intelligent_windows.aspx. However, rotating a piece of glass is limited by the increase in surface area provided by whatever the diameter of the glass is. It takes the thin layer of debris and spreads it out over a bigger area.

U.S. Pat. No. 5,490,912 discloses the use of a roll of transparent tape which is rolled between the laser plasma plume and the laser input window in a PLD system. Transparent tape on a roll has the advantage of having a much larger surface area than a rotating glass window, but it has the disadvantage that the plastic films are typically damaged or distorted by the laser, especially as debris begins to deposit and laser coupling becomes more efficient. Thus the tape must be moved quickly, and the roll must be rather long, with all the mechanical issues that come with it. Also, for use in a high temperature process environment, plastic tapes are unsuitable as they will distort.

The use of an oil to protect and coat the surface of an optical component has been suggested.

Chraplyvy—Applied Optics, Vol. 16, No. 9, September 1977—"Liquid Surface Coating For Optical Components Used In High Power Laser Applications" suggests using viscous paraffin oil and discusses protecting vertical surfaces but to avoid oil running off increases its viscosity until it becomes gel-like. It is not replenished from a bath.

Kessler—International Symposium on Plasma Chemistry, Pugnochiuso, Italy, September 1989—"Direct a-Si:H and a-SiC:H PhotoCVD Deposition with a D2 Lamp and Dielectric Barrier Discharge Lamp" discloses using a coating of Fomblin oil to avoid film deposition on an MgF2 window.

P. Pastorino, G. Morello and S. Tamagno—Journal De Physique IV "Colloque C5, supplement au Journal de Physique 11, Volume 5, June 1995, "Amorphous Hydrogenated Silicon Nitride Deposited Mercury Photosensitization Chemical Vapour Deposition for Optoelectronic Applications" discloses using Fomblin oil on a quartz window of the chamber.

In both Kessler and Pastorino the Fomblin oil was used in a horizontal configuration, and when the oil is dissociated by the VUV photons it has to be replaced, or the window darkens. No oil bath is used.

SUMMARY

According to the present invention there is provided a self-cleaning optical system for the transmission or reflection of light to and/or from a process region, the system comprising a liquid bath and a transparent or reflective optical component continuously rotatable about a non-vertical axis so that a lower part of the component continuously rotates through the bath, whereby as the component emerges from the bath a coating of the liquid remains thereon which forms a substantially uniform film on at least a part of the component through which the light is transmitted or from which the light is reflected.

The optical component may be contained within a vacuum housing, the vacuum housing having an opening which is vacuum sealable to a mating opening in a vacuum chamber in which the process takes place, and wherein an external wall of the vacuum housing has a transparent window through which the light passes on its way to or from the part of the component having the substantially uniform film.

Alternatively the optical component may form an external wall of a vacuum housing, the vacuum housing having an opening which is vacuum sealable to a mating opening in a vacuum chamber in which the process takes place.

Preferably the optical component is circularly symmetric and the axis of rotation passes through its centre of symmetry.

In certain embodiments the centre of the component is mounted to a spindle which rotates the component. In other embodiments the component is rotated by its edges.

The liquid in the bath may coat only one side or may coat both sides of the optical component.

In various embodiments the optical component is a flat transparent circular plate, a lens, a mirror, and a transparent cylinder.

The system may include means for cooling and/or heating the liquid in the bath.

The light may be laser light and the process may be a vacuum process.

In certain embodiments the liquid is an oil having a kinematic viscosity less than 2,000 centistokes.

The invention is applicable to pulsed laser EUV light sources in which high power lasers are used to produce EUV light from laser plasmas. The laser plasma also produces debris in large quantities, a part of which goes back along the laser path and spoils the laser input window. The oil-coated window keeps the transmission of this system substantially constant.

The invention is also applicable to pulsed laser deposition where, similar to the EUV sources, the PLD laser is focused on a surface to produce a plume which is useful for deposition. The laser entrance window is also susceptible to damage from debris here.

In plasma deposition and etching systems process windows allow systems performance to be optically monitored. This is typically by looking at the spectrum of the optical emission from a plasma process, or optical absorption through the plasma, or using microscopy or ellipsometry or other optical techniques on the substrate being treated, to monitor the progress of the etch or deposition process. If this window gets spoiled it can reduce the quality of the optical process monitoring. The invention allows for a consistent transparency of a window into the process chamber, which would otherwise be spoiled quickly.

Another application of the invention is to laser machining systems. In such systems it is advantageous to use low f-number optics to produce the smallest possible laser focal spot at the substrate surface, to produce the smallest possible features on the surface. Low f-number optics have to be either far from the surface with a high optic diameter, and consequently a high laser beam diameter which normally requires expensive beam expansion optics, or closer to the workpiece surface with consequently smaller less expensive optics and beam diameters being required. The disadvantage of being closer to the workpiece is that more debris is deposited on the optics, destroying them more quickly. The invention can be used in front of the optics in a laser machining system protecting otherwise fragile optics and allowing for more cost effective machining, with less downtime for optics replacement and repair.

In general the invention can be used in any situation where laser or optical paths need to be protected from large amounts of debris to maintain optical throughput. The embodiments considered here relate to EUV light sources (laser plasma and laser assisted discharge plasma), and pulsed laser deposition, but other plasma processes which would benefit from constant optical monitoring would also benefit.

The invention could also be used for optical monitoring of any coating process, even outside a vacuum, where inspection windows and windows in optical monitors are prone to spoiling.

BRIEF DESCRIPTION OF THE DRAWINGS

Embodiments of the invention will now be described, by way of example, with reference to the accompanying drawings, in which.

In the various figures of the drawings the same or equivalent components have been designated by the same reference numerals.

DETAILED DESCRIPTION

Figure 1:
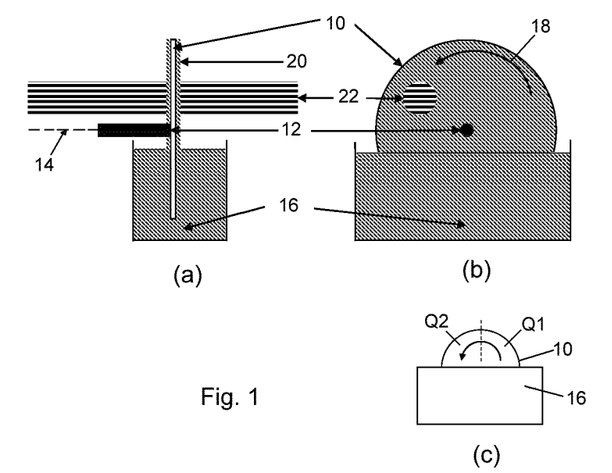
FIGS. 1(a) and 1(b) are schematic side and end views of a self-cleaning optical window system according to a first embodiment of the invention.
FIG. 1(c) illustrates the non-uniform and uniform oil film quadrants in the system of FIGS. 1(a) and 1(b).

Referring to FIG. 1, a first embodiment of the invention comprises a transparent glass plate 10 in the form of an optically flat circular disc. The plate 10 is mounted vertically to a spindle 12 for rotation in its own plane about a horizontal axis 14 passing through the centre of the plate. The plate 10 may be made of glass, quartz, CaF2, MgF2, LiF or other transparent material according to circumstances.

A lower portion of the plate 10 dips into a bath 16 of transparent oil. In operation a motor (not shown) continuously rotates the spindle 12—as indicated by the arrow 18—so that the lower half of the plate 10 continuously rotates through the oil. Oils which can be used, depending on circumstances, are fluorocarbon polymers oils, fluorocarbon polymers of polyhexafluoropropylene oxide, low vapour pressure polyphenyl ether, and other low pressure oils.

As the plate 10 emerges from the bath 16 a thin coating 20 of the oil remains on the glass. Initially, as the plate 10 leaves the oil bath 16, the coating 20 does not have a sufficiently uniform thickness for use as an optical window; this corresponds generally to the ¼ of the plate 10 in the position of the quadrant Q1 in FIG. 1(c). However, by the time the part of the plate 10 initially occupying quadrant Q1 has rotated to the position of quadrant Q2 the oil coating 20 has evened out to form a film of substantially uniform thickness several tens of microns thick, usable as an optical window. Thus a light beam 22 which is transmitted to, and/or received from, a region in which a physical and/or chemical process is taking place (such region being located at the right hand side of FIG. 1(a) but not shown) is therefore directed to pass though the part of the plate 10 in quadrant Q2. Depending on the application, the light beam 22 may be laser light or incoherent light from a thermal source or any photons from any source which are required to be transmitted through the window, and which fall within the transmission range of both the plate substrate material 10 and the oil film coating 20.

The oil film protects the underlying glass plate 10 from the debris of the process. This debris is included in the oil and brought back into the oil bath 16 by rotation of the plate, where it is diluted (and flushed away if the oil in the bath is replaced).

By flushing the debris into the oil bath, the useful lifetime of the window can be increased by thousands of times. If the oil is flushed and/or filtered then this lifetime can be even longer, and the environment in which it is working can be even dirtier, enabling processes which could not be attempted previously, for example, with PLD, enabling laser machining processes with low f-number optics close to the dirty process area, and enabling optical monitoring of processes which were previously too dirty.

The laser passes substantially unabsorbed by the oil through the rotating window, and the system can operate for tens of hours without any window replacement or cleaning, whereas without the rotating oil coated window one could typically operate for less than a minute.

The important oil parameters are:

I) The kinematic viscosity, optimised so that a reasonable rotation rate can be maintained through the bath to replenish the oil, whilst maintaining a high quality optical transmission (i.e. an optically flat film) on a large enough portion of the window to be useful. For most applications this kinematic viscosity should be below 2,000 centistokes. It may be possible to use more viscous transparent oils in a situation where the replenishment rate does not have to be high because the damage process to the window is slow. In relation to rotation rates, in one example, a window with a diameter of 150 mm is rotated at a rate of about 5 rpm to transmit about 75 watts of 1064 nm wavelength 3 kHz repetition rate laser with a pulse energy of about 25 mJ and a pulse length of less than 10 nanoseconds. The laser beam going through the window has a diameter of about 25 mm, and this passes through the window with the centre of the laser pulse located about 25 to 30 mm from the edge of the glass, in the quadrant Q2 described above. This gives sufficiently high quality transmission to allow the laser to be focussed to produce a plasma which emits EUV photons (12 nm to 16 nm in this case) over a plasma diameter of less than 30 microns. With a bath containing 50 ml of oil, such a system can be run for many hours while maintaining window transparency.

II) The relative surface energies of the oil, plate and process gas environment, optimised so that effective wetting of the oil over the surface of the plate is achieved. In practise we have found that oils with a surface tension of <35 milliNewton/meter (or dyne/cm) at 25 deg C give best wetting on a range of optically transparent materials at pressure levels from atmosphere to high vacuum (<10 e-7 millibar). In practise PFPE (perfluoropolyether) oils have the best wetting properties of low vapour pressure oils which are suitable for use in the self-healing window described above. In applications where fluorine contamination at any level is unacceptable silicone oils are an alternative low vapour pressure oil, with sufficiently good wetting properties.

III) Vapour pressure is a parameter which will have greater or lesser importance depending on the application. For very low vapour pressure applications PFPE (perfluoropolyether) oils with a vapour pressure below 10 e-11 mbar at 25 deg C are available, with kinematic viscosity below 2000 centistokes at 25 deg C, and a surface tension of below 35 mN/m at 25 deg C, which allow the self-cleaning window system described above to be used at these very low pressures. This is of advantage where the window system is being used in a vacuum environment where contamination of optical components or other system components such as process coatings must be kept to a minimum.

Fluorinated polymer oils (such as PFPE (Perfluoropolyether)), have the properties of low surface tension, and low viscosity that make them ideal for the present system. They can also have very low vapour pressure, so that they do not contaminate the system too much, and they have very low reactivity rates so they do not break down easily in the presence of reactive species, and they also transmit photons over a wide wavelength range from the mid-infrared down to the vacuum ultraviolet (down to and below 150 nm).

Figure 2:
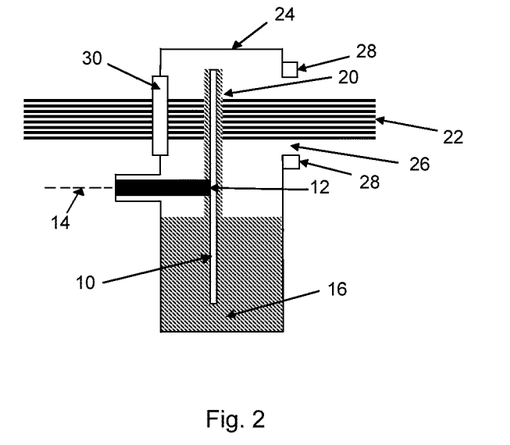
FIGS. 2 to 6 are schematic side views of self-cleaning optical window systems according to second to sixth embodiments of the invention.

In a second embodiment, FIG. 2, the plate 10 and bath 16 is contained within a vacuum housing 24. The vacuum housing 24 has an opening 26 which is vacuum sealable by a vacuum flange connector 28 to a mating opening in a vacuum chamber (not shown) in which a vacuum process is taking place. In this case an external wall of the vacuum housing 24 has a fixed transparent window 30 through which the light 22 passes on its way to or from the part of the plate 10 having the substantially uniform oil film, the light also passing through the opening 26.

This arrangement allows the window system to be mounted and dismounted easily from a more complex vacuum system in which a vacuum process is taking place. Alternatively, the entire window system could also be contained within the vacuum system where the process is taking place.

Figure 3:
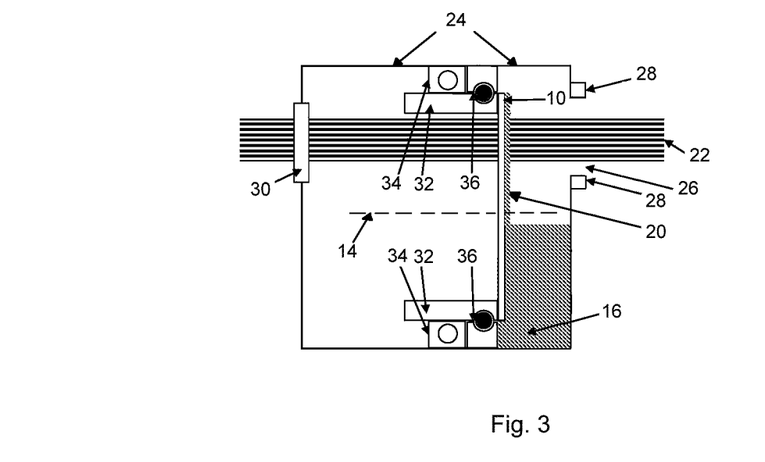

In a third embodiment, FIG. 3, the plate 10 is mounted by its peripheral edge to a cylinder 32 in the vacuum housing 24, the cylinder 32 being in turn mounted in a ring bearing 34 for rotation by a motor (not shown) about the axis 14. The rotational accuracy of the bearing 34 allows the plate 10 to be rotated with minimal wobble, and allows the laser and/or light beam 22 entering and/or exiting to do so with minimal spatial displacement over time. Of course, a spindle 12 could be used if desired. An oil seal 36 between the vacuum housing 24 and the cylinder 32 allows for only one side of the plate 10 to be coated with oil. This has the advantage of producing a protective coating only on the side of the plate 10 facing the process chamber where it is prone to damage. The other side has no oil coating, and so can have better optical performance including flatness and optical transmission and antireflection coating.

Figure 4:
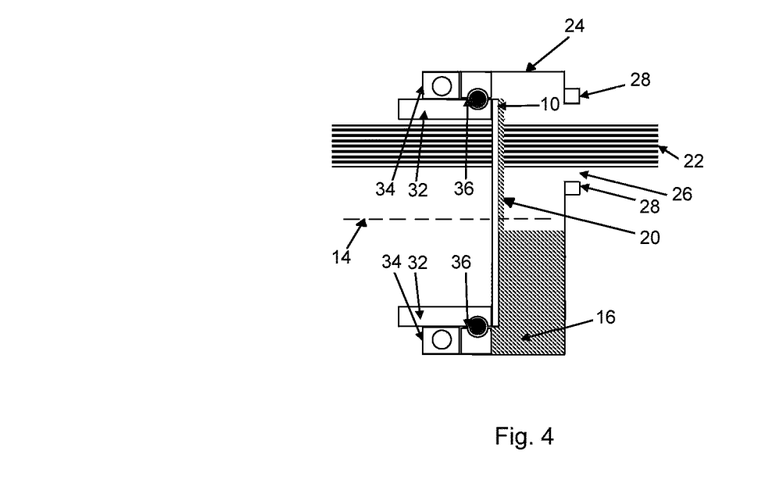

If the bearing 34 and/or the oil seal 36 includes a vacuum seal, or if a separate vacuum seal (not shown) is provided, the portion of the vacuum housing 24 to the left of the plate 10 may be omitted, as shown in the embodiment of FIG. 4. This also renders the window 30 unnecessary.

The invention can also be applied to curved glass surfaces including lenses so long as the lens can be used off axis and still provide adequate focusing properties. Focusing with off axis spherical/aspheric lenses can achieve high laser spot quality and if the lens is coated on at least one side then it can be protected directly from debris by the oil. The lens will have a useful area of one quadrant, analogous to the useful quadrant Q2 of the window in FIG. 1(c). A typical embodiment of this is shown in FIG. 5, the flat plate 10 being replaced by a lens 100 which focusses the light 22 at a point 40 within the process region (alternatively, the light 22 may be coming from the process region).

The invention can also be used to protect a mirror to maintain reflectivity, both on flat and curved mirrors, so long as only a portion of the mirror is required for the optical process. This system would be of particular advantage in a system where femtosecond laser pulses are being used in for machining, or plasma process, as the increased optical path through refractive optics which can distort ultrashort femtosecond laser pulses can be avoided, and the oil coating will only add some tens of microns of material to the beam path. The laser beam will reflect off the underlying mirror material and the oil will protect the mirror material from debris damage.

Figure 6:
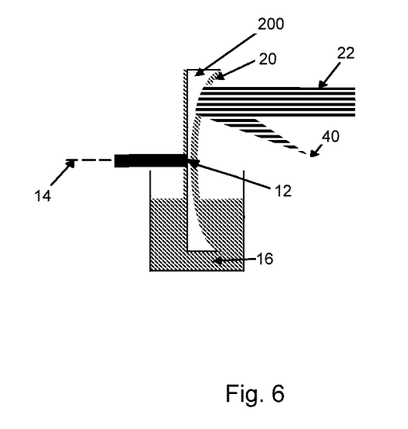

An embodiment of this is shown in FIG. 6, where a mirror 200 is used instead of the flat plate 10. The mirror may be flat, convex or, as shown, concave. In this case the light 22 is reflected by the mirror.

Figure 5:
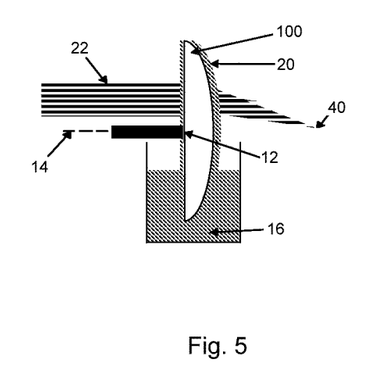

In both FIG. 5 and FIG. 6 a coating of oil remains on the optical component (i.e. lens or mirror) as it rotates through the bath 16 and the light 22 is transmitted or reflected at a position where the oil coating 20 has evened out to form a film of substantially uniform thickness.

In both FIGS. 5 and 6 the optical component 100 or 200 can be rotated by its edges rather than via a spindle, and the system can be located in a vacuum housing similar to that shown in FIG. 2, 3 or 4.

The invention can also be used in a configuration where the window is a hollow transparent cylinder, and the light comes through the curved side of the cylinder to or from a process region inside the hollow portion of the cylinder. This would have the advantage of being more economical in space terms in certain applications where space was important.

Figure 7:
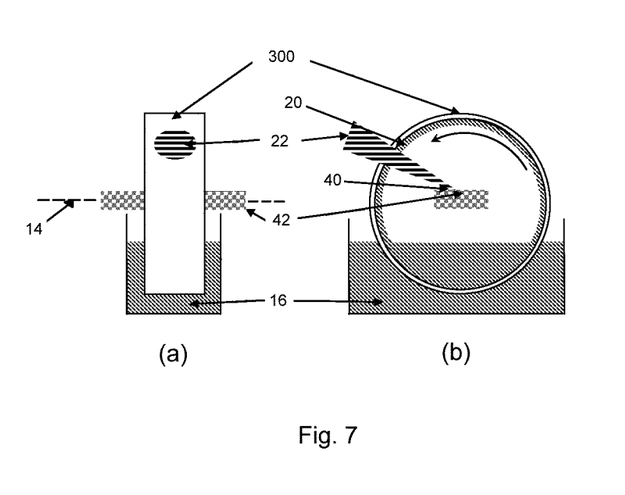
FIGS. 7(a) and 7(b) are schematic side and end views of a self-cleaning optical window system according to a seventh embodiment of the invention.

An example is shown in FIG. 7. Here the optical window is in the form of a transparent glass cylinder 300 coaxial with and rotatable about the axis 14 by a motor (not shown). The cylinder 300 picks up a coating of oil 20 as it rotates through the bath 16 and the light 22 is transmitted at a position where the oil coating 20 has evened out to form a film of substantially uniform thickness. The oil may coat one or both of the internal and external surfaces of the cylinder 300 (only the internal surface is shown coated in FIG. 7). For example, if the oil is desired to coat only the internal surface of the cylinder 300 the oil bath may be formed by the cylinder itself being partially filled with oil, the oil being prevented from escaping by providing segmental walls which slidingly engage and are oil-sealed against opposite sides of at least the lower part of the cylinder. Another alternative is to have an annular rim on each side of the cylinder which would contain the oil up to the rim depth, which would form a pool at the bottom of the cylinder and coat the internal surface of the cylinder with oil. In FIG. 7 the process region is within the cylinder and in the example shown the light 22 is shown focussed on a bar 42 of material under investigation. In other embodiments the light 22 may be coming from the process region. If desired the system shown in FIG. 7 could be located in a vacuum housing.

Considering again the characteristics of the oil, the useful kinematic viscosity range is less than 2000 cSt for laser applications. This viscosity will determine the film thickness and stability at rotation rates which will be high enough so that the laser does not deform the film, reducing optical quality. If the viscosity is too high, then as the rotation rate is increased and the surface does not have time to become flat over half a rotation, which it is required to do. This low viscosity can be reached by heating an oil which has too high a viscosity at lower temperatures to be useful. Providing that the hot oil remains transparent to the laser and that its vapour pressure at the useful temperature is acceptably low, and that its surface tension and the surface energy of the glass plate can be kept compatible with uniform wetting at this elevated temperature, then an oil with a high ambient temperature viscosity could be used.

Thus the oil has to be kept at a temperature that is high enough to have appropriate viscosity/wetting characteristics (which in the case of fluoropolymer oils is room temperature), and low enough so that it doesn't out-gas and spoil whatever vacuum or process chamber that it is in (which with certain fluoropolymer oils is about 50 deg C).

Given that the oil has to be kept in a particular temperature range, specific to the oil and plate surface, and that in use the plate will have the heat load of the laser or plasma process to dissipate, then temperature control of the oil will be required (perhaps both heating and cooling). For particular process parameters cooling of the oil can be designed, as outlined below.
  (a) pass a length of water cooled metal tubing through the oil.
  (b) allow atmospheric cooling by making the vacuum housing 24 of a metal, so that thermal conduction to the ambient air takes place.
  (c) as (b) above, but supplemented by a water cooling loop attached to the exterior surface of the metal wall.

It would also be possible to have a flow of cooled oil passing through the bath to maintain the required temperature, and having a flow of oil would also facilitate filtering of the oil, and constant addition of clean oil to maintain window transparency over an extended period.

Although the forgoing has used oil as the liquid in the cleaning bath, any suitable liquid with the correct wetting/vapour pressure/viscosity parameters for a given application can be used. For example, water has a relatively low vapour pressure at room temperature for some processes, it wets some substrates reasonably well, and it is highly transparent over a good range of wavelengths.

In certain embodiments, the thickness of the oil film may additionally be controlled by rollers or blades (not shown) as appropriate.

In certain embodiments, the thickness of the oil film may be controlled such that an interference anti-reflection coating or partial anti-reflection coating is produced for at least one wavelength passing through the optical system, at least at one angle with respect to the window normal. This would typically require that the thickness of the oil film be approximately an odd integer number of quarter wavelengths of the light for which an anti-reflection property is required.

In certain embodiments, in addition or as an alternative to the above-mentioned roller or blade, a blade or brush (not shown) could be applied to the surface of the transparent optical component at a place submerged fully under the liquid in order to remove any particulates or debris attached to the rotating substrate and include them in the oil volume, where they do not reduce the optical quality of the window system and from where they can be easily filtered or left to sediment to the bottom of the bath.

The invention is not limited to the embodiments described herein which may be modified or varied without departing from the scope of the invention.

The invention claimed is:

1. A self-cleaning optical system for the transmission or reflection of light to and/or from a process region, the system comprising a bath which is arranged to, in use, contain a liquid, and a transparent or reflective optical component arranged to continuously rotate about a non-vertical axis so that, in use, a lower part of the component continuously rotates through liquid contained in the bath and whereby as the component emerges from the bath a coating of the liquid remains thereon which forms a substantially uniform transparent film on at least a part of the component through which transparent film the light is transmitted or from which the light is reflected back through the transparent film.

2. An optical system as claimed in claim 1 wherein the optical component is contained within a vacuum housing, the vacuum housing having an opening which is vacuum sealable to a mating opening in a vacuum chamber in which the process takes place, and wherein an external wall of the vacuum housing has a transparent window arranged so that, in use, light passes through the window on its way to or from the part of the component having the substantially uniform transparent film.

3. An optical system as claimed in which 1 wherein the optical component forms an external wall of a vacuum housing, the vacuum housing having an opening which is vacuum sealable to a mating opening in a vacuum chamber in which the process takes place.

4. An optical system as claimed in claim 1 wherein the optical component is circularly symmetric and the axis of rotation passes through its centre of symmetry.

5. An optical system as claimed in claim 4 wherein the centre of the component is mounted to a spindle which rotates the component.

6. An optical system as claimed in claim 1 wherein the component is rotated by its edges.

7. An optical system as claimed in claim 1 wherein the bath is configured so that, in use, liquid in the bath either coats only one side; or coats both sides of the optical component.

8. An optical system as claimed in claim 1 wherein the optical component comprises one of: a flat transparent circular plate, a lens, a mirror or a transparent cylinder.

9. An optical system as claimed in claim 1 further including means for cooling and/or heating the liquid in the bath.

10. An optical system as claimed in claim 1 wherein said light comprises laser light and the process is a vacuum process.

11. An optical system as claimed in claim 1 wherein the liquid is an oil having a kinematic viscosity less than 2,000 centistokes.

12. An optical system as claimed in claim 1 further including a pulsed laser EUV light source.

13. An optical system as claimed in claim 1 further including an additional mechanism for controlling the thickness of said liquid coating.

14. An optical system as claimed in claim 2 wherein said system is configured to maintain the thickness of said liquid such that an at least partial anti-reflection coating is produced for at least one wavelength passing through the optical system, at least at one angle with respect to the window normal.

15. An optical system as claimed in claim 1 further including a mechanism at least partially disposed beneath the surface of the liquid in the bath and arranged to be applied to the surface of the optical component to remove any particulates from the component.

16. A pulsed laser deposition system incorporating the optical system of claim 1.

17. A laser machining system incorporating the optical system of claim 1.

18. A plasma deposition system incorporating the optical system of claim 1.

19. A plasma etch system incorporating the optical system of claim 1.

20. A deposition system incorporating the optical system of claim 1.

* * * * *